United States Patent [19]  
Haus et al.

[11] Patent Number: 4,676,977  
[45] Date of Patent: Jun. 30, 1987

[54] STABILIZED PESTICIDAL EMULSIONS

[75] Inventors: Joseph B. Haus, Montclair; Esther Gombos, Lyndhurst, both of N.J.

[73] Assignee: Roussel Uclaf, Paris, France

[21] Appl. No.: 833,085

[22] Filed: Feb. 24, 1986

Related U.S. Application Data

[63] Continuation of Ser. No. 652,425, Sep. 20, 1984, abandoned, which is a continuation of Ser. No. 392,987, Jun. 28, 1982, abandoned.

[51] Int. Cl.$^4$ .......................... A61L 9/04; A01N 43/08
[52] U.S. Cl. ...................................... 424/45; 514/461; 514/972
[58] Field of Search .................... 424/45; 514/461, 972

[56]  References Cited
U.S. PATENT DOCUMENTS

| | | | |
|---|---|---|---|
| 3,465,007 | 9/1969 | Elliott | 549/497 |
| 3,510,558 | 5/1970 | Hamuro | 514/421 |
| 3,542,928 | 11/1970 | Elliott | 514/461 |
| 3,832,467 | 8/1974 | Nakanishi et al. | 514/461 |
| 4,000,266 | 12/1976 | Incho | 514/461 |

FOREIGN PATENT DOCUMENTS

| | | | |
|---|---|---|---|
| 46-4198 | 2/1971 | Japan | 514/461 |
| 51-35436 | 3/1976 | Japan | 424/45 |
| 2025771 | 1/1980 | United Kingdom | 514/461 |

Primary Examiner—Albert T. Meyers  
Assistant Examiner—John M. Kilcoyne  
Attorney, Agent, or Firm—Bierman & Muserlian

[57] ABSTRACT

The present invention provides stabilized pesticidal emulsions in which (5-Benzyl-3-furyl)methyl 2,2-dimethyl-3-(2-methylpropenyl)cyclopropanecarboxylate may be used as the sole active ingredient or in combination with other pesticidal agents without the development of the unpleasant odor characteristic of that compound.

9 Claims, No Drawings

STABILIZED PESTICIDAL EMULSIONS

PRIOR APPLICATION

This application is a continuation of U.S. patent application Ser. No. 652,425 filed Sept. 20, 1984, now abandoned which in turn is a continuation of U.S. patent application Ser. No. 392,987 filed June 20, 1982, now abandoned.

SUMMARY OF THE INVENTION

The present invention relates to stabilized pesticidal emulsions. In particular, the present invention relates to substantially odor-free pesticidal emulsions comprising in combination, a pesticidal component having as the active pesticidal agent (5-Benzyl-3-furyl)methyl 2,2-dimethyl-3-(2methylpropenyl)cyclopropanecarboxylate in a suitable solvent, and a stabilizing component comprising at least one stabilizing compound selected from the group consisting of sodium carbonate and potassium carbonate, said stabilizing compound being in aqueous solution, and a suitable emulsifier, wherein the proportion of said stabilizing compound present is at least ten percent (10%) by weight of the amount of the pesticidal agent.

BACKGROUND OF THE PRESENT INVENTION

The compound (5-Benzyl-3-furyl)methyl 2,2-dimethyl-3-(2-methylpropenyl)cyclopropanecarboxylate, which is sometimes written as 5-benzyl-3-furylmethyl chrysanthemate, but is more generally known by the generic term Resmethrin. (Either formula name or this generic term may be used interchangeably throughout this specification). This compound is a widely used, broad spectrum insecticide which combines a high insecticidal activity and low mammalian toxicity.

The compound, however, has one significant drawback which has limited its use. The compound is known to give off an unpleasant, urine-like odor after its application. In addition, the odor which is produced is very persistent and remains noticeable for a long period of time, particularly if the compound is used on absorptive surfaces such as rugs, wood paneling or the like.

Conventional odor control methods have been employed to attempt to mask this unpleasant odor. In this regard, perfumed masking agents have been tested, but the masking effect only lasts for a short period of time. The unpleasant odor of Resmethrin typically persists for such a long period of time that any masking effect of such a perfume becomes ineffective.

This unpleasant odor is readily detected after exposure to sunlight, or even bright artificial light. Antioxidants, ultraviolet screening sunscreens, oxidizing and reducing agents have been suggested to prevent light-induced decomposition. Some of these agents have been successful in delaying the on-set of the typical unpleasant, urine-like odor. In this regard, British Specification No. 1,429,437 shows the addition of 2,2-methylene bis-(6-tert-butyl-4-ethylphenol), known to be an anti-oxidant, to render the odor of Resmethrin less unpleasant. Also disclosed as optional UV-absorbers were 4-tert-butylphenyl salicylate or 2-hydroxy-4-methoxybenzophenone.

The unpleasantness and persistance of this odor has limited the specific uses for which Resmethrin is generally acceptable. Further, these problems have limited the use of Resmethrin in general purpose insecticidal compositions. Such compositions typically contain two or more specific purpose insecticides in combination. For example, such compositions frequently contain synthetic pyrethoids, variously known as Allethrin (the allyl homolog of cinerin I available commercially from Rousell-Uclaf), Bioallethrin (d-trans-allethrin available commercially from Fairfield American Corp.), Neopynamin (tetramethrin commercially available from Sumitomo), or other pyrethrins, all of which are known to have good "knockdown" activity, and are therefore particularly useful in household sprays for flying insects. Such compounds, when combined with Resmethrin and, preferably, a synergist such as piperonyl butoxide produce a useful, general purpose House and Garden-type aerosol with good knockdown and killing power. Such compositions would be expected to have a greater general acceptance if the odor problems associated with Resmethrin could be overcome.

OBJECTS OF THE PRESENT INVENTION

It is an object of the present invention to improve the acceptability of 5-benzyl-3-furylmethyl chrysanthemate as a broad spectrum insecticide.

It is a further object of the present invention to improve the acceptability of 5-benzyl-3-furylmethyl chrysanthemate as a component in general purpose insecticide compositions.

It is a still further object of the present invention to stabilize pesticidal compositions containing 5-benzyl-3furylmethyl chrysanthemate to prevent the formation of unpleasant odor.

The other objects, features and advantages of the present invention will become more apparent in light of the following detailed description of the preferred embodiment thereof.

According to one embodiment of the present invention, there are provided substantially odor-free pesticidal emulsions comprising, in combination, a pesticidal component having as the active pesticidal agent (5-Benzyl-3-furyl)methyl 2,2-dimethyl-3-(2-methylpropenyl)-cyclopropanecarboxylate in a suitable solvent, a stabilizing component comprising at least one stabilizing compound selected from the group consisting of sodium carbonate and potassium carbonate, said stabilizing compound being in aqueous solution, and a suitable emulsifier, wherein the proportion of said stabilizing compound present is at least 10 percent (10%) by weight of the amount of the pesticidal agent.

According to another embodiment of the present invention, there are provided substantially odor-free pesticidal emulsions comprising, in combination, a pesticidal component having at least two active pesticidal agents, one of which agents is (5-Benzyl-3-furyl)methyl 2,2-dimethyl-3-(2-methylpropenyl)cyclopropanecarboxylate in a suitable solvent, a stabilizing component comprising at least one stabilizing compound selected from the group consisting of sodium carbonate and potassium carbonate, said stabilizing compound being in aqueous solution, and a suitable emulsifier wherein the proportion of said stabilizing compound present is at least ten percent (10%) by weight of the amount of (5-Benzyl- 3-furyl)methyl 2,2-dimethyl-3-(2-methylpropenyl)cyclopropanecarboxylate, and the pH of the emulsion is less than 10.0.

According to a further embodiment of the present invention, there is provided a method of preparing substantially odor-free pesticidal emulsions, which method comprises the steps of preparing a pesticidal component having as the active pesticidal agent (5-Benzyl-3-furyl)-methyl 2,2-dimethyl-3-(2-methylpropenyl)cyclopropanecarboxylate by dissolving said pesticidal agent in a suitable solvent, preparing a stabilizing component having at least one stabilizing compound selected from the group consisting of sodium carbonate and potassium carbonate, by dissolving said stabilizing compound in at least a sufficient quantity of water, and combining, in the presence of a suitable emulsifier, said pesticidal component and said stabilizing component in such proportion that the amount of said stabilizing compound represents at least ten percent (10%) by weight of the amount of said pesticidal agent.

According to a still further embodiment of the present invention, there is provided a method of preparing a substantially odor-free pesticidal emulsion comprising the steps of preparing a pesticidal component having at least two active pesticidal agents, one of which is (5-Benzyl-3-furyl)methyl 2,2-dimethyl-3-(2-methylpropenyl)cyclopropanecarboxylate, by dissolving said pesticidal agents in a suitable solvent, preparing a stabilizing compound having at least one stabilizing compound selected from the group consisting of sodium carbonate and potassium carbonate, by dissolving said stabilizing compound in at least a sufficient quantity of water, combining in the presence of a suitable emulsifier said pesticidal component and said stabilizing component in such proportion that the amount of said stabilizing compound represents at least ten percent (10%) by weight of the amount of (5-Benzyl-3-furyl)methyl 2,2-dimethyl-3-(2-methylpropenyl)-cyclopropanecarboxylate, and adjusting the pH below 10.0, if necessary, to prevent decomposition of any pesticidal agent, with a suitable buffering agent.

DETAILED DESCRIPTION OF THE PRESENT INVENTION

This application is related to another, filed contemporaneously herewith, and having a common assignee. The compositions disclosed in both applications employ the pesticidal agent (5-Benzyl-3-furyl)methyl 2,2-dimethyl-3-(2-methylpropenyl)cyclopropanecarboxylate. As noted above, this compound is sometimes written as 5-benzyl-3-furylmethylchrysanthemate, but is more generally known by the generic term Resmethrin.

Resmethrin is soluble in various organic solvents, but insoluble in water. It is commonly sold as a 40% concentrate in an aromatic solvent. Solvents normally employed for this purpose include those commercially available from the Amoco Chemical Co. under the registered trademark "Panasol AN-2"(aromatic solvent 93%) from the Tenneco Oil Co. under the registered trademark "Tenneco 500-100", (mixed xylene and $C_9$ aromatics 100%) and from Exxon Inc. under the registered trademark "Aromatic 150" (aromatic solvent 98%). These compositions are generally then formulated as an emulsion with water and pressurized to provide insecticidal aerosols.

As noted above, the unpleasant odor produced by Resmethrin is readily detected after exposure to sunlight or bright artificial light. Studies of degradation products of Resmethrin have shown that one of the minor photo-decomposition products is phenylacetic acid. Additional studies have shown that it is the presence of this compound which accounts for the unpleasant, urine-like odor. Only a small amount of phenylacetic acid is produced in the decomposition of Resmethrin. However, organoleptic testing procedures have shown that as little as one part per trillion of phenylacetic acid in the air can be detected by odor panels. Obviously, to avoid the unpleasant odor, prevention of the formation of phenylacetic acid must be substantially complete.

It has now been found, surprisingly, that sodium carbonate or potassium carbonate, when present in the aqueous phase of Resmethrin emulsions will prevent the decomposition mechanism of the Resmethrin which yields the objectionable phenylacetic acid odor. Further, it has been found that levels of sodium carbonate or potassium carbonate as low as ten percent (10%) by weight of the Resmethrin, will have this desirable effect. An emulsion prepared in this way may be employed in that form. However, it is believed to be preferable to pressurize the emulsion to provide an insecticidal aerosol.

When utilized in such aerosol sprays, sodium carbonate or potassium carbonate levels which still represent at least ten percent (10%) by weight of Resmethrin, may be as low as one-tenth of one percent (0.1%) by weight of the overall composition, and will prevent the formation of phenylacetic acid. The addition of one percent (1.0%) sodium carbonate to a typical aqueous pressurized spray of Resmethrin will increase the pH of the composition to about 11.0, but the Resmethrin appears to remain substantially stable at such elevated pH levels. At levels of sodium carbonate or potassium carbonate above about three-tenths of one percent (0.3%) by weight of the composition, however, the elevated pH begins to show an effect on unprotected aerosol can linings. For this reason it appears preferable to limit the proportion of stabilizing sodium carbonate or potassium carbonate to levels which will represent between one-tenth of one percent (0.1%) by weight and three-tenths of one percent (0.3%) by weight of such aerosol compositions. Treatment of the aerosol can linings to prevent the effects of higher pH will allow use of sodium carbonate or potassium carbonate at higher levels.

In order to determine if the advantage of the stabilizing agents employed in the present invention was merely a function of increased pH, similar samples were prepared combining Resmethrin with one percent (1.0%) sodium hydroxide (pH 12), one percent (1.0%) sodium borate (pH 10) and one percent (1.0%) triethanolamine (pH 10). None of these formulations prevented the characteristic unpleasant odor of Resmethrin. In addition, a sample was prepared combining Resmethrin with one percent (1.0%) sodium bicarbonate. The resulting composition, with a pH of 8.0, demonstrated reduced, but still objectionable odor.

Although Resmethrin is an excellent broad spectrum insecticide, it is known to lack the quick "knockdown" properties required in a household spray for flying insects. As noted earlier, synthetic pyrethoids, variously known as Bioallethrin, Allethrin, Neopynamin or other pyrethrins are all known to have such "knockdown" characteristics. The combination of any of these compounds with Resmethrin, preferably with a synergist such as piperonyl butoxide, will produce a general purpose House and Garden-type spray having good knockdown and kill. Further, the present invention will provide the benefits of such a spray without the problems associated with the unpleasant odor caused by the phenylacetic acid which is created when Resmethrin begins to photo-decompose. This is accomplished in the following manner.

In order to prevent the decomposition of Resmethrin in such combination compositions, an amount of sodium carbonate, potassium carbonate or some combination of the two, is added in aqueous solution, representing at least ten percent (10%) of the amount of Resmethrin. This composition would be expected to have a fairly high pH, on the order of about 11.0. At such a level any of the various knockdown ingredients set out above would be expected to decompose quickly. This decomposition may be prevented by the addition of a sufficient amount of a buffering agent, such as sodium bicarbonate or monobasic sodium phosphate to maintain the pH below 10.0, preferably, lower the pH to approximately 8.5 to 9.0. Since sodium bicarbonate appears to be marginally effective in preventing the odor-causing decomposition, it is believed to be the preferred buffering agent. Preferably, the total amount of stabilizing agent and buffering agent should be no more than fifteen one-hundredths of one percent (0.15%) of the total aerosol composition in the practice of this embodiment.

Various emulsifying agents may be employed in the compositions of the present invention. The amounts necessary will be dependent on the purpose to be served by the various compositions. Thus, compositions to be used immediately after preparation will require little emulsification, while compositions intended to be shelf stable must be adequately protected from phase separation. Emulsifiers which will serve these purposes are well known to the art.

Emulsifiers normally employed for this purpose include those commercially available from the Witco Chemical Company, sold under the trade name Witconol 14, and from the Stepan Chemical Co., sold under the trade name Toximul D. These emulsifiers are generally formulated with water and combined with the other components of the invention to form an emulsion. The resulting emulsion can then be pressurized to provide insecticidal aerosols.

The present invention is shown more clearly in the following illustrative examples.

EXAMPLE 1

One and twenty-five one hundredths gram (1.25 g.) of a 40% Resmethrin concentrate in a commercially available aromatic solvent, equivalent to one-half gram (0.5 g.) of Resmethrin, was placed in an aerosol container. To this concentrate was added seventy-five one-hundredths of a gram (0.75 g.) of an emulsifier, commercially available from the Witco Chemical Co., and sold under the trade name Witconol 14, (polyglycerol ester of oleic acid) one-half gram (0.5 g.) of a corrosion inhibitor, commercially available from Swift & Co., and sold under the trade name Epoxol 9-5; (substance prepared by epoxidation of unsaturated oil and esters) and sixty-two and five-tenths grams (62.5 g.) of deionized water containing thirty-six one-hundredths of a gram (0.36 g.) of sodium carbonate in solution. An aerosol valve was then attached and the container was charged with thirty-five grams (35 g.) of isobutane.

The aerosol composition thus prepared was tested on glass and carpet surfaces. None of the unpleasant odor typical to phenylacetic acid developed, even after exposure to direct sunlight. Glass and carpet surfaces sprayed with a control aerosol formulated in the same manner, but without the sodium carbonate, produced the strong, unpleasant, urine-like odor typical of phenylacetic acid within several hours.

EXAMPLE 2

One-half gram (0.5 g.) of the same 40% Resmethrin concentrate representing two-tenths gram (0.2 g.) Resmethrin and fifteen one-hundredths of a gram (0.15 g.) of Bioallethrin, a synthetic pyrethroid commercially available from Roussell-Uclaf, were placed in an aerosol container. To these components was added one gram (1.0 g.) of Witconol 14, seventy-five one-hundredths of a gram (0.75 g.) of Epoxol 9-5 as in the previous example. In addition, sixty-seven and six-tenths gram (67.6 g.) deionized water, containing seventy-two one-thousandths of a gram (0.072 g.) of sodium carbonate and seventy-two one-thousandths of a gram (0.072 g.) sodium bicarbonate in solution was added. An aerosol valve was then attached and the container was charged with thirty grams (30 g.) of an 87%–13% mixture of isobutane and propane.

The aerosol composition thus prepared was tested and did not present an odor problem. Tests with a control aerosol formulated in the same manner, but without the sodium carbonate produced the strong, unpleasant, urine-like odor typical of phenylacetic acid within several hours.

EXAMPLE 3

Twenty-five one hundredths of a gram (0.25 g.) of the same Resmethrin concentrate representing one-tenth gram (0.1 g.) Resmethrin, two-tenths of a gram (0.2 g.) of Allethrin, a synthetic pyrethoid commercially available from Fairfield American Corp., and eight-tenths of a gram (0.8 g.) of piperonyl butoxide, also commercially available from Fairfield American Corp., were placed in an aerosol container. As in the previous examples, to this mixture was added eight-tenths of a gram (0.8 g.) of Witconol 14 and seven-tenths of a gram (0.7 g.) of Epoxol 9-5. In addition, sixty-seven and twenty-five one hundredths gram (67.25 g.) of deionized water, containing seventy-two one-thousandths of a gram (0.072 g.) of sodium carbonate and seventy-two one-thousandths of a gram (0.072 g.) of monobasic sodium phosphate in solution, was added. An aerosol valve was then attached and the container was charged with thirty grams (30 g.) of an 87%–13% mixture of isobutane and propane.

The aerosol composition produced was tested on glass plates which were exposed to direct sunlight. None of the unpleasant odor typical of phenylacetic acid developed. Glass plates sprayed with a control aerosol formulated in the same manner, but without the sodium carbonate and monobasic sodium phosphate, produced the strong, unpleasant, urine-like odor typical of phenylacetic acid within several hours.

EXAMPLE 4

Sixty two grams of the same 40% concentrate, representing twenty-five grams (25 g.) of Resmethrin, and eight grams (8.0 g.) of emulsifier, commercially available from the Stepan Chemical Co., under the trade name Toximul D, (amber-colored blend of calcium alkylbenzene sulfonates, nonionic surfactants, and fluidizing solvents) were dissolved in a sufficient quantity of aromatic solvent, commercially available from the Amoco Chemical Co., under the trade name Panasol AN-2, to make up one hundred grams (100 g.) of an emulsifiable concentrate.

A first sample, designated as Sample A, was prepared by diluting one gram (1.0 g.) of this emulsifiable concentrate with ninety-nine grams (99 g.) of water containing twenty-five one-hundredths of a gram (0.25 g.) of potassium carbonate in solution. A second sample, designated as Sample B, was prepared by diluting one gram (1.0 g.) of the same emulsifiable concentrate with ninety-nine grams (99 g.) of plain water.

Each of these samples were applied onto carpet squares which were then placed on a windowsill in bright sunlight. No odor was detected from the carpet square sprayed with Sample A, while the carpet square sprayed with Sample B produced the strong, unpleasant, urine-like odor typical of phenylacetic acid within several hours.

The other features, advantages and specific embodiments of this invention will become readily apparent to those exercising ordinary skill in the art after reading the foregoing disclosures. These specific embodiments are within the scope of the claimed subject matter unless otherwise expressly indicated to the contrary. Moreover, while specific embodiments of this invention have been described in considerable detail, variations and modifications of these embodiments can be effected without departing from the spirit and scope of this invention as disclosed and claimed.

What is claimed is:

1. An odor-free insecticidal emulsion comprising in combination, an insecticidal component having as the active insecticidal agent (5-Benzyl-3-furyl)-methyl 2,2-dimethyl-3-(2-methylpropenyl)-cyclopropane-carboxylate in an aromatic solvent, a stabilizing component comprising at least one stabilizing compound selected from the group consisting of sodium carbonate and potassium carbonate, said stabilizing compound being in aqueous solution, and an emulsifier, wherein the proportion of said stabilizing compound present is at least ten percent (10%) by weight of the amount of the insecticidal agent.

2. An odor-free insecticidal emulsion comprising in combination, an insecticidal component having at least two active insecticidal agents, one of which agents is (5-Benzyl-3-furyl)-methyl 2,2-dimethyl-3-(2-methylpropenyl)-cyclopropanecarboxylate, and the second of which is a different synthetic pyrethroid, in an aromatic solvent, a stabilizing component comprising at least one stabilizing compound selected from the group consisting of sodium carbonate and potassium carbonate said stabilizing compound being in aqueous solution, and an emulsifier, wherein the proportion of said stabilizing compound present is at least ten percent (10%) by weight of the amount of (5-Benzyl-3-furyl)-methyl 2,2-dimethyl-3-(2-methyl- propenyl)-cyclopropanecarboxylate, wherein the pH of the emulsion is between 8.5–9 further characterized in that said pH range is maintained by a buffer selected from the group consisting of sodium bicarbonate and monobasic sodium phosphate.

3. The insecticidal emulsion of claim 1 or 2 in the form of a dilute and pressurized aerosol preparation.

4. The insecticidal emulsion of claim 1 or 2 in the form of a dilute and pressurized aerosol preparation, and further characterized in that the stabilizing compound represents no more than one percent (1.0%) of the overall aerosol composition.

5. The insecticidal emulsion of claim 1 or 2 formulated with said insecticidal component to form a 40% concentrate solution.

6. A method of preparing a substantially odor-free pesticidal emulsion comprising the steps of:
preparing a pesticidal component having as the active pesticidal agent (5-Benzyl-3-furyl)methyl 2,2-dimethyl-3-(2-methylpropenyl)cyclopropanecarboxylate by dissolving said pesticidal agent in a suitable solvent,
preparing a stabilizing component having at least one stabilizing compound selected from the group consisting of sodium carbonate and potassium carbonate, by dissolving said stabilizing compound in at least a sufficient quantity of water, and
combining in the presence of a suitable emulsifier said pesticidal component and said stabilizing component in such proportion that the amount of said stabilizing compound represents at least ten percent (10%) by weight of the amount of said pesticidal agent.

7. A method of preparing an odor-free insecticidal emulsion comprising the steps of: preparing an insecticidal component having at least two active insecticidal agents, one of which agents is (5-Benzyl-3-furyl)-methyl 2,2-dimethyl-3-(2-methylpropenyl)-cyclopropanecarboxylate, and the second of which is a different synthetic pyrethroid, by dissolving said insecticidal agents in an aromatic solvent, preparing a stabilizing component having at least one stabilizing compound selected from the group consisting of sodium carbonate and potassium carbonate, by dissolving said stabilizing compound in at least a sufficient quantity of water, combining in the presence of an emulsifier said insecticidal component and stabilizing component in such proportion that the amount of said stabilizing compound represents at least ten percent (10%) by weight of the amount of (5-Benzyl-3-furyl)-methyl 2,2-dimethyl-3-(2-methylpropenyl)-cyclopropanecarboxylate and adjusting the pH to a range between 8.5–9, if necessary, to prevent decomposition of any insecticidal agent with a buffering agent selected from the group consisting of sodium bicarbonate and monobasic phosphate.

8. The method of claim 7 in which the buffer employed is sodium bicarbonate.

9. The method of claim 7 in which the buffer employed is monobasic sodium phosphate.

* * * * *

UNITED STATES PATENT AND TRADEMARK OFFICE
CERTIFICATE OF CORRECTION

PATENT NO. : 4,676,977
DATED     : June 30, 1987
INVENTOR(S) : Joseph B. Haus et al It is certified that error appears in the above-identified patent and that said Letters Patent is hereby corrected as shown below:

On the title page assignee should read

--(73) Assignee: BIO-UCLAF S.A.
                 Wilmington, De. --.

Signed and Sealed this

Twenty-second Day of December, 1987

Attest:

DONALD J. QUIGG

*Attesting Officer*                *Commissioner of Patents and Trademarks*